United States Patent [19]

Shibata et al.

[11] Patent Number: 5,310,673

[45] Date of Patent: May 10, 1994

[54] MASS PROPAGATION THROUGH SHOOT PRIMORDIA AND REGENERATION OF PLANTS FROM PROTOPLASTS OF SHOOT PRIMORDIA

[75] Inventors: Masaru Shibata, Kameyama; Kazuya Ito, Yokkaichi; Keigo Doi, Kameyama; Masaki Ito, Yokkaichi, all of Japan

[73] Assignee: Oji Paper Company, Ltd., Tokyo, Japan

[21] Appl. No.: 917,677

[22] Filed: Jul. 22, 1992

Related U.S. Application Data

[63] Continuation of Ser. No. 453,388, Dec. 15, 1989, abandoned, which is a continuation of Ser. No. 63,871, Jun. 19, 1987, abandoned.

[30] Foreign Application Priority Data

Jun. 26, 1986 [JP] Japan .................. 61-148282
Jun. 2, 1987 [JP] Japan .................. 62-137647

[51] Int. Cl.$^5$ .................. C12N 5/02; C12N 5/00
[52] U.S. Cl. .................. 435/240.47; 435/240.45; 435/240.49; 435/240.54
[58] Field of Search .................. 435/240.45, 240.47, 435/240.49, 240.54

[56] References Cited

FOREIGN PATENT DOCUMENTS

| 59-132822 | 7/1984 | Japan | A01G 1/00 |
| 59-132823 | 7/1984 | Japan | A01G 1/00 |
| 61-192283 | 8/1986 | Japan | C12N 5/00 |
| 62-55020 | 3/1987 | Japan | A01G 1/00 |

OTHER PUBLICATIONS

Smith et al. 1982/1983 Plant Science Letters 28:149–156.
Wolter, K. 1968, Nature 219:509–510.
Vasil et al. 1980, Theor. Appl. Genet. 56:97–99.
Vasil et al. 1983, Z. Pflanzenphysiol. 111:233–239.
Russell et al. 1986, Plant Science 46(2):133–142.
McCown, B. 1985, TAPPI J. 68(5):116–119.
de Vries et al. 1986, J. Plant Physiol. 122(3):199–203.
Tanaka et al. 1983, Proc. Japan Acad., Ser. B., 59(10):359–362.
Tanaka et al. 1985, Jpn. J. Genet. 60:405–410.
Krikorian et al. 1984, pp. 338–341 In: Handbook of Plant Cell Culture, vol. 2, Sharpe et al., eds., Macmillan, N.Y.
Russell et al. 1987, Biol. Abstr. 83(5):#43319.
Conner et al. 1984, Plant Cell Tissue Organ Culture 3:59–68.
R. Tanaka et al., Jpn. J. Genet. 58, 65–70, 1983.

*Primary Examiner*—David T. Fox
*Attorney, Agent, or Firm*—Armstrong, Westerman, Hattori, McLeland & Naughton

[57] ABSTRACT

A process for the mass-propagation of a woody plant comprising the steps of removing a shoot tip from the woody plant, transplanting the shoot tip to an artificial medium containing inorganic salts and plant growth hormones as main ingredients, and rotary-culturing the shoot tip under illumination to form shoot primordia, and stationary-culturing the shoot primordia in a liquid medium to regenerate shoots. Further, a process for the regeneration of plants comprising the steps of preparing a shoot primordium by rotary-culturing a shoot tip of a plant, treating the shoot primordium with at least one enzyme to prepare a protoplast, culturing the protoplast in an artificial medium containing plant hormones and inorganic and organic salts as main ingredients to form a callus, and incubating the callus in a regeneration medium to regenerate a shoot; plus intermediate materials of the process, and processes for production of the intermediate materials.

2 Claims, 2 Drawing Sheets

MASS PROPAGATION THROUGH SHOOT PRIMORDIA AND REGENERATION OF PLANTS FROM PROTOPLASTS OF SHOOT PRIMORDIA

This application is a continuation of application Ser. No. 07/453,388 filed Dec. 15, 1989 (now abandoned), which is a continuation of Ser. No. 07/063,871, filed Jun. 19, 1987 (now abandoned).

BACKGROUND OF THE INVENTION

1. Field of the Invention

The present invention generally relates to a process for a mass-propagation and regeneration of plants from protoplasts of shoot primordia. More specifically, it relates to a process for a mass-production of woody plants through shoot primordia, and a process for a regeneration of plants from protoplasts of shoot primordia.

2. Description of the Related Art

The propagation process for woody plants is classified into two fundamental processes, i.e., sexual reproduction, and asexual reproduction, including cutting and tissue culture. In the sexual reproduction of allogamous plants, the traits of parent plants are not necessarily transmitted to their progeny, due to pollen variations. In the cases of interspecific hybrid and $F_1$ hybrid generated by hybrid vigor as well as polyploid plant, the genotype of parent plant cannot be transmitted to its progeny without change.

The asexual reproduction includes cutting, which has been extensively used for a long time as a propagation method for excellent plants. However, cutting is not appropriate for the propagation of woody plants, due to a lower propagation rate, lower rooting ability, the necessity of a field for production of plant pieces for cutting, and a limited season for cutting. On the other hand, the tissue culture methods have recently been rapidly developed. There are disadvantages in that a mass-propagation of progeny plants having the same traits as the parent plant is difficult because chromosomal aberration and gene mutation occur at a high frequency during the regeneration of shoots from calli. Moreover, in many cases, the long-term subculture of callus lowers its differentiation potency.

More specifically, for broad-leaved trees such as poplar, eucalypt and the like, there have been attempts at mass-propagation using culture of various kinds of organs, such as shoot tip, axillary bud, cotyledon, hypocotyl, stem etc. However, when starting from the shoot tip, since once a callus is induced from the shoot tip and the callus is then redifferentiated into shoots, the same problem occurs. On the other hand, in the case of direct induction of adventitious shoot from stem or the like, i.e., micropropagation, continuously to obtain shoots, the stems or the like must be planted at appropriate intervals, resulting in a disadvantage in commercial mass-propagation.

Moreover, for gymnosperms such as conifer, it is possible to generate an embryoid. For example, Mostafa M. et al. (U.S. Pat. No. 4,217,730 issued on Aug. 19, 1980) prepared embryoid from *Pseudotsuga menziesii* by suspension culture. In this method, although the regeneration-term is shorter than in conventional tissue culture (organogenesis), a rate of the conversion of the embryoid into an entire plant is as low as 15 to 50%. Another disadvantage of this method is that, since young cotyledons are used, a large amount of seeds is necessary. Therefore, this method does not form a seedless mass-propagation process for excellent individuals.

Accordingly, in the conventional tissue culture, a genetically stable and rapid mass-propagation technique for woody plants has not been accomplished.

Recently, for the propagation of annual plants other than woody plants, a "shoot primordium" method was presented (Ryuso Tanaka et al., *Jpn. J. Genet.* Vol. 58, 65-70, 1983; Japanese Unexamined Patent Publication No. 59-132822; and Japanese Unexamined Patent Publication No. 59-132823).

This shoot primordium method is a method using shoot tip. In this method, shoot tips are removed from an annual plant, and the shoot tips are rotary-cultured in an artificial medium under a particular temperature, illumination, and rotation rate to form globular cell aggregates containing shoot primordia, which are then cultured for shooting to obtain for a short term a large amount of young plants stably maintaining the genetic traits of their parent.

The present inventors found that the "shoot primordium" method, which has already been applied to annual plants such as water-melon, maize, rice, morning glory, Swertia, Papaver and the like, is also applicable to perennial woody plants (Japanese Unexamined Patent Publication No. 62-55020).

Shoot primordium is a propagation body, and by propagating the shoot primordia a large number of clones can be produced from a parent plant via the shoot primordia.

In the shoot primordium method, so far shoot primordia are stationary-cultured for shooting on a solid medium such as agar medium. In this stationary-culture, however, the shooting ratio is as low as about 30%.

Since a protoplast has no cell wall, it is capable of cell fusion or useful genes can be introduced therein. If plants can be regenerated from a protoplast thus manipulated, it is possible to create novel plants, for example, plants providing a higher yield and better taste, and exhibiting a greater resistance to pest and bad weather conditions, and so on. In herbaceous plants, many kinds of species are capable of regeneration from protoplasts. However, for woody plants, a regeneration of protoplast into plant is successful only in limited kinds of plants, such as "Trovita" orange (Kobayashi, S. et al., *Jpn. J. Breeding*, Vol. 34, supplement 2, 32-33, 1984), paper mulberry (Oka, S. and K. Oyama, *Jpn. J. Breeding*, Vol. 34, supplement 2, 26-27, 1984; Japanese Unexamined Patent Publication No. 61-192283), poplar (Ito, K. et al. the present inventors, Japanese Patent Application No. 61-64800; Russell, J.A. and B.H. McCown, *Plant Sci.*, 46, 133-142, 1986), Sandalwood (Rao, R.S. and P. Ozias-Akins, *Protoplasma*, 124, 80-86, 1985) and Ulmus (STICKLEN, M.B. et al., *Plant Sci.*, 47, 29-34, 1986).

A reason for this may be that isolated protoplasts excrete substances such as polyphenols into a medium during culturing, and the excreted substances have an adverse affect on the survival and cell division, resulting in an inhibition of the regeneration of the plant.

To overcome this obstacle, recently, principally for monocotyledon, an immature embryo or an inflorescence is used to form an embryogenic callus, and from the callus, protoplasts are prepared and cultured to regenerate plants. However, this method is disadvantageous in that the preparation of a starting material is time-consuming, the method can be carried out only in a limited season, and it is difficult to provide stable materials due to genetic mutation occurring during the callus formation.

Therefore, it is desirable to develop those materials which are genetically stable, have differentiation ability, and can propagate in a large amount.

SUMMARY OF THE INVENTION

Accordingly, the present invention provides a process for a mass-production of woody plants through shoot primordia, as well as a process for regeneration of plants from protoplasts of shoot primordia.

More specifically, the present invention provides a process for a mass-propagation of a woody plant comprising the steps of:

removing a shoot tip from the woody plant;

transplanting the shoot tip to an artificial medium containing inorganic salts and plant growth hormones as main ingredients, and rotary-culturing the shoot tip under illumination to form shoot primordia; and stationary-culturing the shoot primordia in a liquid medium to regenerate shoots.

The present invention also provides protoplast derived from shoot primordium by eliminating the cell wall thereof.

The present invention moreover provides a process for a production of protoplast comprising the steps of:

preparing shoot primordia;

treating the shoot primordia with at least one enzyme; and separating protoplasts.

Moreover, the present invention provides a process for a formation of callus comprising the steps of:

preparing shoot primordia;

treating the shoot primordia with at least one enzyme to prepare protoplasts; and culturing the protoplast in an artificial medium containing plant hormones and inorganic salts as main ingredients to form a callus.

Moreover, the present invention provides a process for a regeneration of plant comprising the steps of:

preparing shoot primordia by rotary-culturing a shoot tip of a plant;

treating the shoot primordia with at least one enzyme to prepare protoplasts, culturing the protoplasts in an artificial medium containing plant hormones and inorganic acids as main ingredients to form a callus; and incubating the callus in a regeneration medium to regenerate shoots.

DESCRIPTION OF THE PREFERRED EMBODIMENTS

Figure 1:
FIG. 1 is a photograph showing appearance of shoots obtained by stationary culture of shoot primordia of poplar in a liquid medium according to Example 1.

According to one embodiment of the present invention, to mass-propagate a woody plant in genetically stable state, shoot tips are sterilized and removed from the woody plant, and transferred to an artificial medium containing inorganic salts and plant growth hormones as main ingredients, and rotary-cultured under illumination to form shoot primordia, and the shoot primordia are then stationary-cultured in a liquid medium containing inorganic salts and plant growth hormones as main ingredients to regenerate plants.

The woody plants to which the present process can be applied include, but are not limited to, evergreen broad-leaved trees such as eucalypt, acacia, caoutchouc tree, coffee; deciduous broad-leaved trees such as poplar, Quercus, oak, Japanese lacquer; fruit trees such as orange, lemon, apple, pear, peach, avocado, kiwi-fruit, persimmon, walnut, grape, fig, almond, and mango; and flower trees such as rose, camellia, ume (Japanese apricot), and cherry.

Preparation of shoot primordium

Shoot apexes are removed from a woody tree, sterilized in a sterilizing solution, and washed thoroughly with sterilized water. Under a stereo-microscope, shoot tips are aseptically removed from the sterilized shoot pieces, and the shoot tips are transplanted to an artificial liquid medium containing inorganic salts and plant growth hormones. If necessary or preferable, the liquid medium is supplemented with a differentiation-stimulating organic substance such as coconut milk.

The composition of inorganic and organic salts contained in the artificial liquid medium varies depending on the kinds of plant to be treated, but fundamentally will be a modified Gamborg's B5 medium (abbreviated as B5 medium hereinafter).

The plant growth hormones include auxins such as naphthalene acetic acid (NAA), 2,4-dichlorophenoxyacetic acid (2,4-D), indole-3-acetic acid (IAA), indole-3-propionic acid (IPA), indole-3-butylic acid (IBA), phenylacetic acid (PAA), benzofuran-3-acetic acid (BFA), phenylbutylic acid (PBA) and the like; and cytokinins such as 6-benzylaminopurine (BA), kinetin, KT-30 (Kyowa Hakko, Japan), zeatin (Z) and the like.

The rotary culture is carried out at a constant temperature of between 15° C. and 30° C., preferably 25° C. and 30° C. At a lower temperature, the propagation is delayed; and at too high a temperature the growth is poor and unstable.

The illumination is carried out preferably continuously at a strength of 2,000 to 20,000 lux using a fluorescent lamp. A higher or lower strength of illumination has an adverse affect on the growth of the shoot primordia.

The rotary-culture is essential to ensure a sufficient growth of the shoot primordia; that is, in a stationary-culture, only a poor growth of shoot primordia can be obtained.

For the rotary culture, for example, a rotary culturing apparatus (Nippon Ika Kikai Seisakusho, Japan) having a rotating circular plate of a diameter of about 100 cm is used. Test tubes containing a medium into which a shoot tip is transplanted are attached to the rotating circular plate in such a manner that the tubes are parallel with a rotation axis of the circular plate and the tubes constantly face in the same direction during the rotation of the circular plate. The tubes are illuminated from upside. The rotation rate of the circular plate is preferably as low as 0.5 to 5 rpm. Too high a rotation rate provides much callus, and too low a rotation rate provides much precocious branch, both resulting in a poor shoot primordia formation.

When the present propagation method is applied to poplar, eucalypt and acacia, actively growing shoot primordia are obtained, and the resulting shoot primordium is hemispherical. The shoot primordium of poplar and eucalypt is a green-block having a callus at its basal portion. The shoot primordia of acacia is a blackish-purple having a callus at its basal part. Note, these shoot primordia have continued to propagate for 19 to 21 months, and are still actively propagating.

The shoot primordium has, at its early state, a smooth surface which has projections having a diameter of 40 to 70 μm. The projection comprises small polyhedral cells which divide vertically, tangentially, obliquely, and in other ways. The shoot primordium at this stage (primary shoot primordium) becomes gradually longer, and when the diameter thereof reaches 200 to 1,000 μm, the shoot primordium differentiates into two layers, i.e., epidermal system and cortex system. The outermost layer comprises one or two cell layers for which only periclinal division is observed. The inner layer present inside the outermost layer comprises a large number of rather large cells, and in these cells, a large number of well-developed chloroplasts, vacuole and storage granules are observed. Moreover, the shoot primordium at this stage (secondary shoot primordium) has a trapezoid rise having a diameter of 400 to 2,000 μm. At this stage, several primary shoot primordia newly generate from the circumferential surface of the trapezoid rise. Through the above-mentioned steps, the number of shoot primordia increases four fold for one month. Note, in the case of subculturing shoot primordia once a month, the mutation rate is as extremely low as on an order of $10^{-6}$, and the same as the natural mutation rate. This means that the present shoot primordium method provides a rapid and genetically stable mass-propagation of plants.

Shooting of shoot primordium

Shoot primordia thus grown are then stationary-cultured in a liquid shooting medium similar to the medium used for shoot primordia formation, at 15° C. to 30° C. and under illumination at a strength of 1,000 to 4,000 lux, to form a large number of small shoots. Next, the shoots are transplanted to a rooting medium for rooting of the shoots, resulting in entire plants. About three months must pass from the start of the stationary culture to form an entire plant. The resulting plants are completely identical to their parent in genotype, chromosome type, and phenotype.

According to a second embodiment of the present invention, shoot primordia are treated with enzyme to isolate protoplasts, the protoplasts are cultured in an artificial medium containing inorganic salts and plant growth hormones as main ingredients, and then the callus is cultured in a regeneration medium to generate plants.

Plants to which the present method can be applied include, but are not limited to, evergreen broad-leaved trees such as eucalypt, acacia, caoutchouc tree, and coffee; deciduous broad-leaved trees such as poplar, paulownia, Quercus, oak, Japanese lacquer; useful conifers such as pine, Japanese cedar, Japanese cypress, fir, spruce, Japanese larch; fruit trees such a orange, lemon, apple, peach, avocado, kiwi-fruit, persimmon, walnut, grape, fig, almond, and mango; and flower trees such as rose, camellia, ume (Japanese apricot), and cherry. Moreover, in addition to the above-mentioned woody trees, herbaceous plants, for example, flowers such as petunia and cosmos; and crops such as tobacco, flax, rice, wheat, tomato, spinach, and soybean are included.

In the present embodiment, shoot primordia can be prepared by the same procedure as described above.

Preparation of protoplast

A predetermined weight of shoot primordia in a "washing solution" containing 2-(N-Morpholino)-ethanesulfonic acid monohydrate (MES) and $CaCl_2 \cdot H_2O$ is homogenized in a homogenizer. The washing solution can contain, in addition to the above-mentioned components, sorbitol, sucrose or glucose as an osmoticum, and polyvinylpyrrolidone or dextransulfate calcium salt as an additive. The homogenate containing crushed shoot primordia is filtered through nylon mesh, and the recovered shoot primordia are thoroughly washed with the washing solution. To the washed material is added an enzyme solution containing a pectin hydrolyzing enzyme such as pectolyase and cellulose hydrolyzing enzyme for digestion of a cell wall such as cellulase, for example, Cellulase Onozuka RS, as well as mannitol, MES and $CaCl_2 \cdot 2H_2O$, and the mixture is shaken at 20° C. to 30° C. for 24 to 48 hours at 20 to 30 rpm, to isolate protoplasts. Macerozyme R-10 as pectin hydrolyzing enzyme and Cellulase Onozuka R-10 as cell wall digestion enzyme also can be used.

Culturing of protoplasts

Protoplasts thus prepared are then cultured in a plant tissue culture medium to form callus. The plant tissue culture medium is selected according to the nature of the protoplast to be cultured, and is, for example, Gamborg's B5 medium, Murashige-Skoog medium or the like, supplemented with plant hormones, i.e., auxin such as naphthalene acetic acid (NAA), 2,4-dichlorophenoxyacetic acid (2,4-D), or indoleacetic acid (IAA), and cytokinine such as benzylaminopurine (BA), kinetin, KT30 or zeatin. The medium may be a liquid medium, or a solid medium such as an agar medium. Additionally, preferably, the medium also contains 0.001 to 0.05% of a supporting agent such as GELRITE ™ (consisting essentially of polysaccharides extracellularly secreted from Pseudomonas elodea), to support protoplasts in a culture vessel. Preferably, culturing is carried out at an early stage in the dark, and culture room is gradually lightened as the protoplasts grow. The temperature for culturing is preferably 20° C. to 30° C., more preferably 25° C. to 28° C.

When an agar medium is used, to the agar medium melted by heating is added separately prepared protoplast suspension, and the medium is cooled to solidify the medium and maintain the protoplasts in suspension.

When a liquid medium is used, it is necessary to prevent a toxic effect by polyphenols excreted by protoplasts, and coagulation of the suspended protoplasts which can have an adverse affect on the cell division and survival of the protoplasts.

The above-mentioned "GELRITE ™" (Kelco, USA) is a material containing as its main ingredient polysaccharides extracellularly secreted from Pseudomonas elodea. By adding GELRITE ™ to a liquid medium at a low concentration, a layer of gelated GELRITE ™ is formed in the bottom of a culture vessel, and protoplasts adhere to and are supported by, said gelated GELRITE ™ layer. Therefore, when the liquid medium is replaced by a fresh medium, the protoplast are not discharged together with the spent medium.

Regeneration of plant

Callus generated from protoplasts as described above is cultured in a regeneration medium, for example, Gamborg's B5 medium, or Murashige-Skoog medium supplemented with plant hormones, i.e., auxin such as naphthaleneacetic acid (NAA) or 2,4-dichlorophenoxyacetic acid (2,4-D), indoleacetic acid (IAA), and cytokinin such as benzylaminopurine (BA), KT-30, kinetin or zeatin, to easily generate shoots and then roots. In such a manner, the entire plant is regenerated from protoplasts.

EXAMPLES

The present invention will now be further illustrated by, but is by no means limited to, the following examples.

EXAMPLE 1

Plant used for experiment

Populus charkowiensis X P caudina, OP-20

Preparation of shoot primordia

Top pieces having a length of about 20 mm were cut from a green branch of an actively growing poplar and sterilized with 70% ethanol for 5 minutes, then with 7-fold diluted sodium hypochlorite solution for 15 minutes, and washed with sterilized water. Next, in a clean, ventilated room, shoot tips including a growing point and having a length of 0.5 to 1 mm were removed from the sterilized pieces using tweezers and a surgical knife under a stereomicroscope. The removed shoot tips were then transplanted to the modified Gamborg's medium having the composition set forth in Table 1.

TABLE 1

Modified Gamborg's B5 Medium for Poplar

| Component | Concentration (mg/l) |
|---|---|
| NaH$_2$PO$_4$.2H$_2$O | 150 |
| KNO$_3$ | 2,500 |
| (NH$_4$)$_2$SO$_4$ | 134 |
| MgSO$_4$.7H$_2$O | 250 |
| CaCl$_2$ | 150 |
| Fe-EDTA | 40 |
| MnSO$_4$.4H$_2$O | 10 |
| H$_3$BO$_3$ | 3 |
| ZnSO$_4$.7H$_2$O | 2 |
| Na$_2$MoO$_4$.2H$_2$O | 0.25 |
| CuSO$_4$.5H$_2$O | 0.025 |
| CoCl$_2$ 6H$_2$O | 0.025 |
| KI | 0.75 |
| nicotinic acid | 1 |
| thiamine-HCl | 10 |
| pyridoxine-HCl | 1 |
| myo-inositol | 100 |
| sucrose | 30,000 |
| naphthaleneacetic acid | 0.02~0.2 |
| 6-benzylaminopurine | 0.2~0.4 |
| (or KT-30) | (0.2) |
| pH | 5.5~5.8 |

Prior to the main experiment, a pre-experiment was carried out to determine a combination of kinds of hormones and their concentrations in artificial medium, which would provide the highest and most stable growth of shoot primordia. The results are set forth in Tables 2 and 3.

TABLE 2

Combination of NAA Concentration and BA Concentration in Artificial Medium for Poplar (mg/l)

| NAA Concentration | BA Concentration | | | | |
|---|---|---|---|---|---|
| | 0.05 | 0.1 | 0.2 | 0.4 | 1.0 |
| 0.02 | | ○ | | ○ | |
| 0.05 | | | | ○ | |
| 0.1 | | | | | |
| 0.5 | | | | | |
| 1.0 | | | | | |

NAA: naphthaleneacetic acid,
BA: 6-benzylaminopurine,
○: effective combination.

TABLE 3

Combination of NAA Concentration and Zeatin Concentration in Artificial Medium for Poplar (mg/l)

| NAA Concentration | Z Concentration | | | | |
|---|---|---|---|---|---|
| | 0.05 | 0.1 | 0.2 | 0.4 | 1.0 |
| 0 | | | | | |
| 0.02 | | | | | |
| 0.2 | | | ○ | | |
| 2.0 | | | | | |
| 4.0 | | | | | |

NAA: naphthaleneacetic acid
Z: zeatin
○: effective combination

Culturing was carried out in 25 ml of the modified B5 medium in a test tube having a diameter of 30 mm and a length of 200 mm at a temperature of 28° C., an illumination intensity of 2,000 to 20,000 lux, and a rotation rate of 2 rpm.

At the 40th day from the start of culturing, green shoot primordia conglomerates having a diameter of about 10 mm were obtained. The growing shoot primordia conglomerate was then divided into conglomerates having a diameter of about 5 to 10 mm, and the divided conglomerate was transplanted to a freshly prepared medium having the same composition as described above. In this way, once shoot primordia conglomerates have been obtained, the number of shoot primordia is increased four-fold each month. Therefore, after an elapse of n months the number of shoot primordia is increased $4^n$-fold (n: number of month after culturing).

Next, the shoot primordia thus obtained was transplanted to a shooting medium.

Shooting of shoot primordia

The shoot primordia culture prepared by rotary culture as described above was set under a temperature of 28° C., an illumination intensity of 1,000 to 4,000 lux (alternating at 16 hours in the light and 8 hours in the dark), and was cultured as a liquid stationary culture. After 3 week culturing, 10 to 15 shoots having a size of 3 to 5 mm were originated per shoot primordium (see FIG. 1).

After an additional 4 weeks of culturing, the shoots grew to a size of 10 to 15 mm and was then cut from its basal portion and transplanted to a rooting medium comprising a half concentration of B5 basal medium (hormones were omitted from the modified B5 medium) supplemented with 6 g/l of agar. The transplanted shoot formed satisfactory roots after three weeks of culturing.

This procedure according to the present invention provided a shooting ratio of 50%. On the other hand, a comparative procedure wherein the shoot primordia were directly transplanted to the agar medium without being subjected to the liquid culture process, provided only a shooting ratio of 30%.

The grown plantlets were transplanted to a pot containing vermiculite, and after adaptation of the plantlets under a low illumination intensity for two weeks, the pot was transferred to a greenhouse, and the plantlets grown to healthy plants according to a conventional method.

EXAMPLE 2

Plant used for experiment

Eucalyptus saligna, E. grandis

Preparation of shoot primordia

Top pieces having a length of about 10 mm were cut from an actively growing branch of a three-year plant, and sterilized with 70% ethanol for 30 seconds, then with a ten-fold diluted sodium hypochlorite solution for 20 minutes, and washed with sterilized water. Shoot tips were removed from the sterilized top pieces and the shoot tips were transplanted to an artificial medium according to the same procedure as described in Example 1 for poplar. The composition of the artificial medium except for the combination of plant hormones was identical to that used for the poplar (Table 1). The combination of plant hormones was determined by a pre-experiment. As shown in Table 4, a combination of 0 to 0.02 mg/1 of naphthaleneacetic acid and 0.02 to 0.2 mg/1 of 6-benzylaminopurine was effective.

TABLE 4

Combination of NAA Concentration and BA Concentration in Artificial Medium for Eucalypt

| NAA Concentration | BA Concentration (mg/l) | | | | |
|---|---|---|---|---|---|
| | 0 | 0.02 | 0.2 | 2.0 | 4.0 |
| 0 | | | ○ | | |
| 0.02 | | ○ | ○ | | |
| 0.2 | | | | | |
| 2.0 | | | | | |
| 4.0 | | | | | |

NAA: naphthaleneacetic acid.
BA: 6-Benzylaminopurine.
○: effective combination.

In the case of eucalypt, 6 months must pass before shoot primordia conglomerates having a diameter of about 10 mm are formed. This term was much longer than that for poplar. However, after this stage, the shoot primordia increased 4-fold each month, which was the same as poplar.

Shooting of shoot primordia

The shoot primordia culture prepared by rotary culture as described above was set under the same condition as described above for poplar to form shoots.

The shoots thus formed were treated according to the same procedure as described for poplar to form roots which grow into plantlets.

This procedure according to the present invention provided a shooting ratio of about 30%. On the other hand, in a comparative procedure wherein the shoot primordia were directly transplanted to the agar medium without the liquid culture, provided a shooting ratio of only 10%.

EXAMPLE 3

Plant used for experiment

Acacia auriculiformis

Preparation of shoot primordia

Top pieces of a length of about 10 mm were cut from an actively growing branch of a three-year plant, and sterilized according to the same procedure as described for eucalypt. The culturing condition was the same as for eucalypt except that the combination of plant hormones in the artificial medium was (1) 0.02 mg/1 of 2,4-dichlorophenoxyacetic acid and 0.02 mg/1 of 6-benzylaminopurine, or (2) 0.02 mg/1 of 2,4-dichlorophenoxyacetic acid and 0.2 mg/1 of 6-benzylaminopurine, and the rotation rate was 2 rpm. The shoot primordia thus obtained were blackish brown. Although about 6 months must pass before shoot primordia conglomerates having a diameter of about 10 mm are formed, after that the shoot primordia increased 4-fold each month, which was same as for poplar.

Shooting of shoot primordia

The shoot primordia culture prepared by rotary culture as described above was set under the same condition as described above for poplar and eucalypt, to carry out a liquid stationary culture for shooting.

This procedure provided a shooting ratio of about 20%. On the other hand, in a comparative procedure wherein the shoot primordia were directly transplanted to the agar medium without the liquid culture, provided a shooting ratio of only 5%.

The shoots thus obtained were rooted according to the same procedure for poplar, and grew to plantlets.

As seen from Examples 1 to 3, according to the present process, it is possible to maintain and propagate woody plants in a vegetative form in a genetically stable state for a period of many years, and when necessary, to efficiently produce a large number of clones of a plant. The propagation rate is very high; i.e., in the case of broad-leaved-trees, it is possible to produce $4^{12}$ of, i.e., $17 \times 10^6$-fold, shoot primordia from one shoot tip in one year.

Although, the present process was explained using broad-leaved trees, the present process, of course, can apply to conifers.

EXAMPLE 4

Plant used for experiment

Populus charkowiensis X P. caudina, OP-20

Preparation of shoot primordia

Top pieces of branch were cut from a poplar, were sterilized with 70% ethanol and a 7-fold diluted sodium hypochlorite solution, and then shoot tips having a length of about 0.5 mm were aseptically removed from the top pieces, and transplanted into Gamborg's B5 medium supplemented with 0.05 mg/1 of naphthaleneacetic acid and 0.4 mg/1 of benzyladenine (pH 5.6). This medium was then subjected to rotary culture at a temperature of 28° C., an illumination intensity of 20,000 lux, and a rotation rate of 2 rpm.

At the 40th day after the start of culturing, green shoot primordia conglomerates having a diameter of about 10 mm were obtained. After three weeks, the grown conglomerate was divided into conglomerates having a diameter of about 5 to 10 mm, subcultured for two weeks, and used to isolate protoplasts.

Isolation and preparation of protoplasts 1 g of shoot primordia which had been subcultured for two weeks was put in 15 ml of a "washing solution" containing 10 mM 2-(N-Morpholino)ethanesulfonic acid monohydrate (MES), 10 mM $CaCl_2 \cdot 2H_2O$ and 13% mannitol (pH 5.6), and the whole was treated with a homogenizer at 20,000 rpm for 10 seconds to form small sections having a size of about 1 mm. The thus treated material was filtered through a nylon mesh to recover a cell fraction, which was then washed twice with the washing solution.

To the washed material was added 20 ml of an enzyme solution containing 1% Cellulase Onozuka RS, 0.05% pectolyase Y-23, 10 mM $CaCl_2 \cdot 2H_2O$, 10 mM MES and 13% mannitol, and incubated in the dark at 20° C. to 30° C., at a shaking frequency of 20 to 30 rpm, for 24 to 48 hours. After the enzyme treatment, the suspension was filtered through a nylon mesh to eliminate non-digested cell blocks, and the filtrate was centrifuged at 100 xg for three minutes to separate protoplasts from the enzyme solution. The protoplasts were then washed with the washing solution and used for further culturing.

Culturing of protoplasts and regeneration of plants

The protoplasts were cultured in a medium having a composition shown in Table 5.

TABLE 5

Composition of Medium for Culturing Protoplasts
(Gamborg's B5 medium)

| Component | Concentration (mg/l) |
|---|---|
| $KNO_3$ | 2,500 |
| $(NH_4)_2SO_4$ | 134 |
| $MgSO_4.7H_2O$ | 250 |
| $MnSO_4.H_2O$ | 10 |
| $ZnSO_4.7H_2O$ | 2 |
| $CuSO_4.5H_2O$ | 0.025 |
| $CaCl_2.2H_2O$ | 150 |
| $CoCl_2.6H_2O$ | 0.025 |
| KI | 0.75 |
| $NaH_2PO_4.H_2O$ | 150 |
| $H_3BO_3$ | 3 |
| $Na_7MoO_4.2H_2O$ | 0.25 |
| FeEDTA | 40 |
| thiamine-HCl | 10 |
| nicotinic acid | 1 |
| pyridoxine-HCl | 1 |
| myo-inositol | 100 |
| (Other component) | |
| NAA | 0.1 |
| BA | 0.5 |
| 2,4-D | 5 |
| sucrose | 10,000 |
| mannitol | 90,000 |
| pH | 5.6 |

First, Gamborg's B5 medium having a two-times concentration was prepared. Also, a Gelrite solution containing 9% mannitol and 0.005% Gelrite (pH 5.6) was prepared, autoclaved, and completely cooled. The protoplast suspension was mixed with the Gelrite TM solution at a volume ratio of 1:1, and 3 ml each of the mixture was poured into a petri dish having a diameter of 6 cm.

The protoplasts were cultured at first in the dark and then in a gradually lightened condition, at 28° C. for 25 days.

The thus-grown protoplasts were sequentially transplanted every 15 days to media containing a reducing concentration of 6, 3, and 0% of mannitol and a reducing concentration of auxins, and 3% of sucrose to form cells. After two months, the callus was transplanted to a shoot regeneration medium containing Gamborg's B5 medium, 0.02 mg/l of naphthaleneacetic acid, 0.02 g/l of benzyladenine, 3% of sucrose and 0.4% of agar, and cultured at 28° C., under a condition of 16 hours in the light and 8 hours in the dark.

Figure 2:
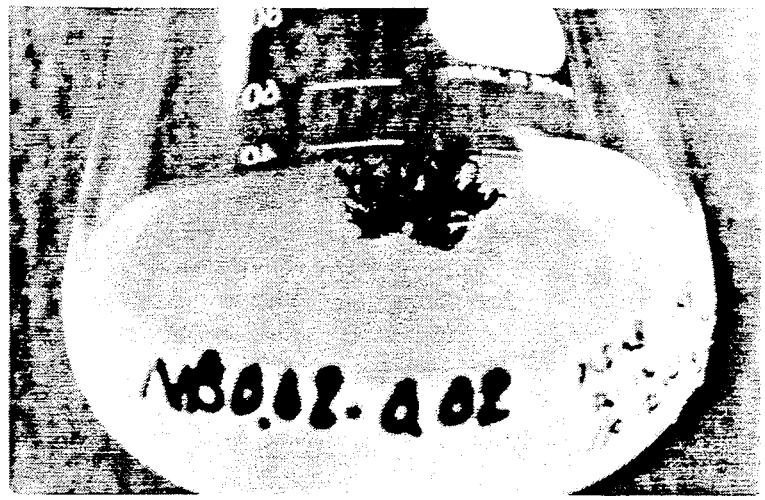
FIG. 2 is a photograph showing shoots regenerated from protoplasts, two weeks after the inoculation of a shoot-regeneration medium with a protoplast culture; and, FIG. 3 is a photograph showing entire plants having both shoots and roots grown from the shoots shown in FIG. 2, two weeks after the transplantation of the shoots into a rooting medium.
Figure 3:

Two weeks after transplanting, the shoots were regenerated as shown in FIG. 2. The shoots were then transplanted to a rooting medium as shown in Table 6 to generate plants having roots as shown in FIG. 3.

TABLE 6

Medium for Rooting

| Component | Concentration (mg/l) |
|---|---|
| Gamborg's B5 medium | |
| (Other component) | |
| NAA | 0 to 0.01 |
| sucrose | 10,000 |
| agar | 4,000 |
| pH | 5.6 |

Comparative Example

A stem of the same mature tree of poplar as used in Example 4 was cut, and the stem was sectioned to make a piece having a length of 2 cm, which was sterilized according to a conventional method, and then peeled to expose cambium. The peeled piece was inserted into a Gamborg's B5 medium supplemented with 0.1 mg/l of naphthaleneacetic acid as an auxin, 0.2 mg/l of benzylaminopurine (or 0.02 mg/l of KT-30) as a cytokinin, 3% of sucrose and 0.8% of agar to form shoots. On the 35th day after the cutting, protoplasts were isolated from the shoots.

That is, the shoot was cut to pieces about 1 mm in length, and the pieces were subjected to the same enzyme treatment and washing as described in Example 4, to isolate and prepare the protoplasts. As a result, $10^6$ protoplasts were obtained from 1 g of the shoot.

When the isolated protoplasts were cultured according to the same procedure as described in Example 4, for two to three days, some of the protoplasts swelled. Although one or two divisions were observed, at the 20th day the protoplasts became brown and coagulated, and, therefore, it was impossible to continue culturing.

As seen from Example 4, although it is very difficult to regenerate plants from protoplasts directly prepared from tissue of woody plants, it became easy to regenerate plants from protoplasts prepared via shoot primordia from a woody plant, and therefore, according to the present invention, a very promising process is provided for creating new breeds of plants.

We claim:

1. A process for regeneration of a poplar plant, the process comprising:
preparing shoot primordia from a poplar plant, said shoot primordia being an aggregation of cells prepared by rotary culture of shoot tips at a temperature of between 15° C. and 30° C. at an illumination strength of between 2,000 and 20,000 lux, and at a rotation rate of between 0.5 and 5 rpm in a medium containing an auxin and a cytokinin;
treating the shoot primordia with at least one enzyme to obtain a protoplast;

culturing the protoplast in a Gamborg's B5 medium containing Gelrite ™ (polysaccharide), naphthaleneacetic acid, benzyladenine and 2,4-dichlorophenoxyacetic acid, and inorganic and organic salts as the main ingredients to form a callus; and incubating the callus in a regeneration medium containing naphthaleneacetic acid and benzyladenine to regenerate shoots.

2. A process according to claim 1, wherein the culturing is carried out at a temperature between 20° C. and 30° C.

* * * * *